United States Patent [19]

Hölscher

[11] Patent Number: 5,647,346
[45] Date of Patent: Jul. 15, 1997

[54] MEDICAL APPARATUS HAVING A METERING DEVICE

[75] Inventor: Uvo Hölscher, Stockelsdorf, Germany

[73] Assignee: Drägerwerk AG, Lubeck, Germany

[21] Appl. No.: 539,959

[22] Filed: Oct. 6, 1995

[30] Foreign Application Priority Data

Oct. 8, 1994 [DE] Germany .................. 44 36 014.2

[51] Int. Cl.⁶ .................................................. A62B 7/00
[52] U.S. Cl. .................. 128/202.22; 128/205.11; 128/204.21; 128/204.18
[58] Field of Search ................ 128/202.22, 205.11, 128/204.21, 204.18, 205.24, 200.23; 364/413.04, 413.03

[56] References Cited

U.S. PATENT DOCUMENTS

| | | | |
|---|---|---|---|
| 4,957,107 | 9/1990 | Sipin | 128/204.21 |
| 4,984,158 | 1/1991 | Hillsman | 128/200.23 |
| 5,237,987 | 8/1993 | Anderson et al. | |
| 5,452,714 | 9/1995 | Anderson et al. | 128/205.11 |

*Primary Examiner*—Vincent Millin
*Assistant Examiner*—William J. Deane, Jr.
*Attorney, Agent, or Firm*—Walter Ottesen

[57] ABSTRACT

A medical apparatus 1 is equipped with: a metering device (2, 3) for a fluid medium (4, 5); a computer unit 19 controlling the metering device (2, 3) according to individual input quantities; a display screen 12 for displaying possible input quantities inside menu structures; a rotatable knob 13 for selecting an input quantity; a pressure-actuated acknowledgment switch 15 for assuming the selected input quantity as a setting value for one of the metering devices 2; and, a further switch 16. This medical apparatus facilitates the correction of incorrectly assumed input quantities. This is provided in that the further switch is configured as a pull switch or slide switch 16 activated by a rotatable knob 13. The pull or slide switch 16 transmits a signal (S1) which cancels the assumption of the input quantity. The signal S1 is transmitted to the computer unit 19 or to the metering device 2 or to both.

4 Claims, 2 Drawing Sheets

MEDICAL APPARATUS HAVING A METERING DEVICE

FIELD OF THE INVENTION

The invention relates to a medical apparatus including: a metering device for a fluid medium, a computer unit for controlling the metering device according to individual input variables, a display screen allowing possible input variables to be shown within menu structures, a rotatable knob for the selection of an input variable, a pressure-actuated acknowledgment switch for assuming the selected input variable as a setting value for the metering device, and a further switch.

BACKGROUND OF THE INVENTION

U.S. Pat. No. 5,237,987 discloses a ventilating apparatus having a mixing and metering device for medical gases for ventilating a patient.

The known ventilating apparatus includes a control arrangement with which the user can set and monitor the ventilating mode and the ventilating gas pressure, the gas composition and the ventilating gas flow. A display screen is a component of the control arrangement with which the parameters set according to the menu structures are displayed to the user as input quantities. In the case that parameters are to be changed, the user can first call up the parameter to be changed in one of the menu structures using a centrally positioned rotatable knob. The parameter to be changed can be selected by pressure on an acknowledgment switch. Inside of a menu window, the parameter can then be varied numerically and the new parameter can now be assumed by the control arrangement as a new setting value for the ventilating apparatus by applying pressure to the acknowledgment switch. Thereafter, another parameter from the menu structure can be selected and changed if required. A further switch enables a switchover between a menu structure that displays parameters and a menu structure that changes parameters.

A disadvantage of the known ventilating apparatus is that, by the numerical change of a selected parameter and inadvertent actuation of the acknowledgment switch, a correction of the parameter assumed in error is not possible directly. Instead, the incorrectly set parameter must first be again selected in order to then be numerically set to the desired value. This complicates handling the apparatus especially in situations of stress.

SUMMARY OF THE INVENTION

The object of the invention is to improve an apparatus of the kind described above so that a simple correction can be made of an incorrectly adopted input quantity as a setting value.

The medical apparatus of the invention includes: a first metering device for metering a first fluid medium; a second metering device for metering a second fluid medium; a display device having a display screen for displaying a first menu structure including a first plurality of input quantities and a second menu structure including a second plurality of input quantities; a computer unit for controlling the metering devices in accordance with individual ones of the input quantities from the menu structures; a rotary knob for selecting one of the input quantities of the first menu structure; a pressure-actuated acknowledgment switch for assuming the selected input quantity as a setting value for one of the metering devices; a pull or slide switch operatively connected to the rotary knob so as to be actuable by the rotary knob to issue a cancelling signal (S1) for cancelling the assumption of the selected input quantity as the setting value; and, circuit means for transmitting the cancelling signal (S1) at least one of the computer unit and the metering devices.

The advantage of the invention lies in the fact that the adoption of a previously changed, new input quantity can be immediately cancelled by pulling or sliding the rotatable knob without involving any further handling steps such as in the form of a repeated selection of the particular input quantity. The manner of actuating the rotatable knob, that is, by pulling or sliding, ensures that the signal cancelling the adoption of the input quantity can only be transmitted deliberately by the user.

In an advantageous embodiment of the invention, it is provided to once again display the same menu structure displayed before the assumption of the quantity on the display screen by means of the signal cancelling the assumption of the input variable. In this manner, an immediate adjustment of the input quantity is possible.

In a further advantageous embodiment of the invention, a medical apparatus includes a computing unit for receiving status quantities, a display screen for displaying possible input quantities for the status quantities within menu structures, a rotatable knob for selecting an input quantity, a pressure-actuated acknowledgment switch for adopting the selected input quantity and a further switch configured in such a way that it is a pull or slide switch actuated by the rotatable knob. It is through this pull or slide switch that a signal S1 cancelling the assumption of the input quantity is transmitted to the computer unit.

The status quantities can be measured variables detected by sensors, for instance, the dosage rate of a medication solution which results from the displacement of a piston actuated by a linear drive. For this purpose, the linear drive can be provided with a position or displacement transducer measuring the displacement of the piston. The input quantities are limit values for the dosage rate that can neither be undershot nor exceeded. Measuring variables alternate to the dosage rate are, for applications in the field of ventilation, for example, the tidal volume, ventilating pressure, breathing frequency, heart rate, oxygen level and the concentration of the anesthetic agent. The input values for these alternate measured variables are the limit values which must be adhered to.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
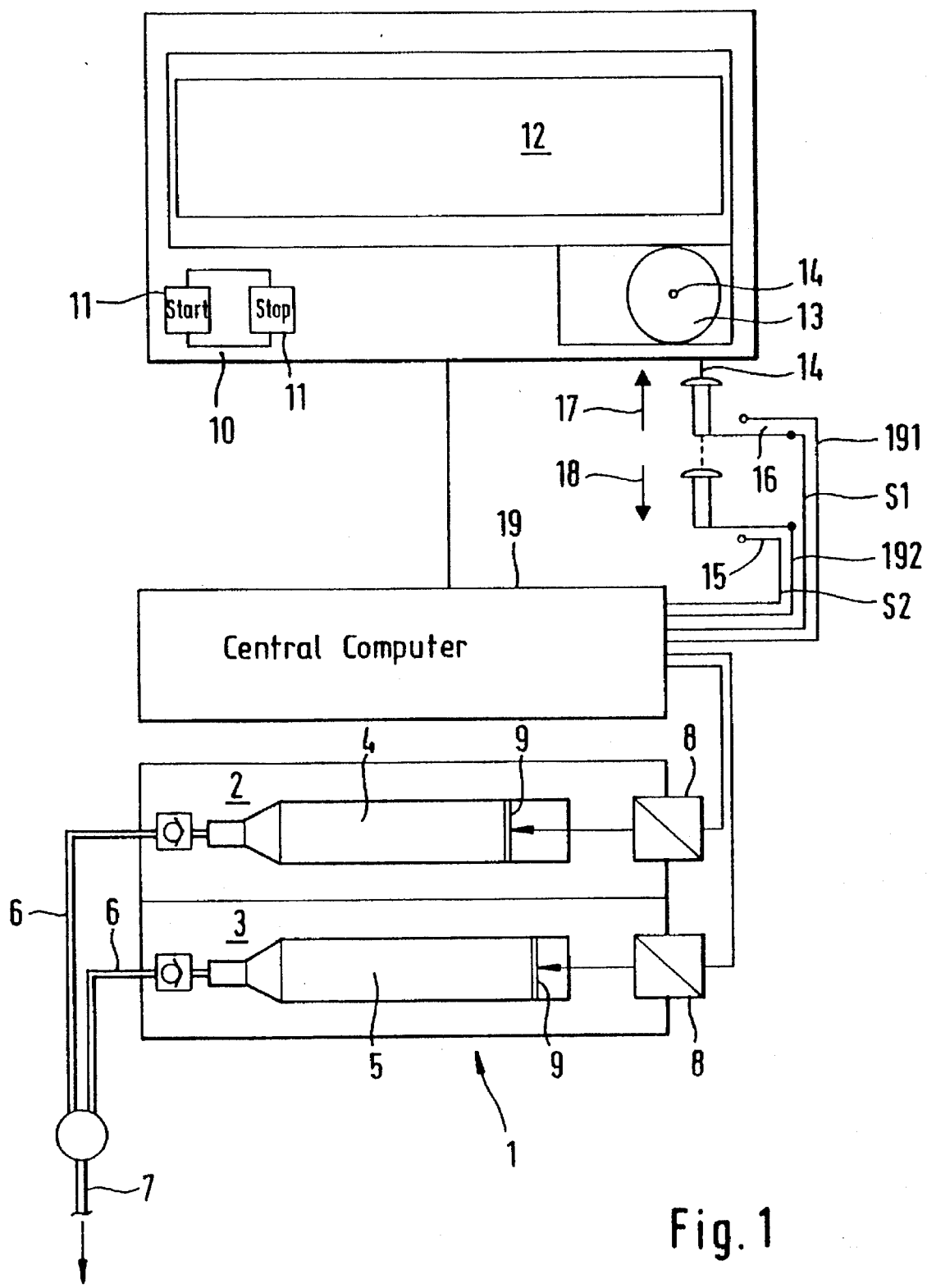
FIG. 1 shows a schematic configuration of a medical apparatus with a metering pump.

FIG. 1 shows schematically the configuration of a medical apparatus 1 having two metering pumps (2, 3) for metering medication solutions (4, 5) via fluid lines 6 into a collecting line 7. The metering pumps (2, 3) are configured as piston pumps and the solutions (4, 5) are transported into their respective fluid lines 6 by means of pistons 9 actuated by linear drives 8. The linear drives 8 each include a displacement measuring device (not shown in FIG. 1) with which the axial displacement of the piston can be detected. The dosage rates of the medication solutions (4, 5) can be determined in a computer unit 19 from the displacemet values of the pistons.

The setting of the input quantities for the metering pumps (2, 3) takes place via a control panel 10 on which various switches 11, a display screen 12 and a rotatable knob 13 are arranged to enable the setting of input values. The rotatable knob 13 is rotatable about a pivot pin 14 which is connected to an acknowledgment switch 15 in the form of a pressure switch and to a pull switch 16. In order to provide a clearer overview, the part of the pin 14, which is positioned behind the control panel 10 and which has been drawn in dotted lines, is folded into the plane of the drawing. In response to a pulling force on the rotatable knob 13 in the direction of the first arrow 17, the pull switch 16 switches to a closed position and pressure on the knob 13 in the direction of second arrow 18 closes the acknowledgment switch 15. The metering is controlled by a microprocessor (not shown in FIG. 1) in the central computer unit 19. Via a first line 191, a first signal S1 can be transmitted to the computer unit 19 by means of the pull switch 16. Via a second line 192, a second signal $2 is transmitted to the computer unit 19 by means of the acknowledgment switch 15. The switches 11 on the control panel 10 enable the metering pumps (2, 3) to be activated or deactivated.

Figure 2A:
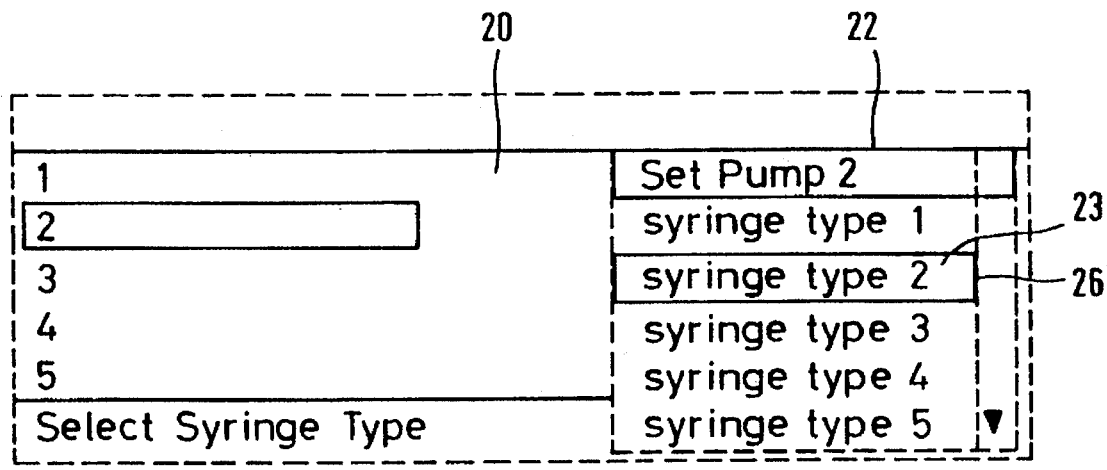
FIG. 2a shows a first menu structure with a first menu window.
Figure 2B:
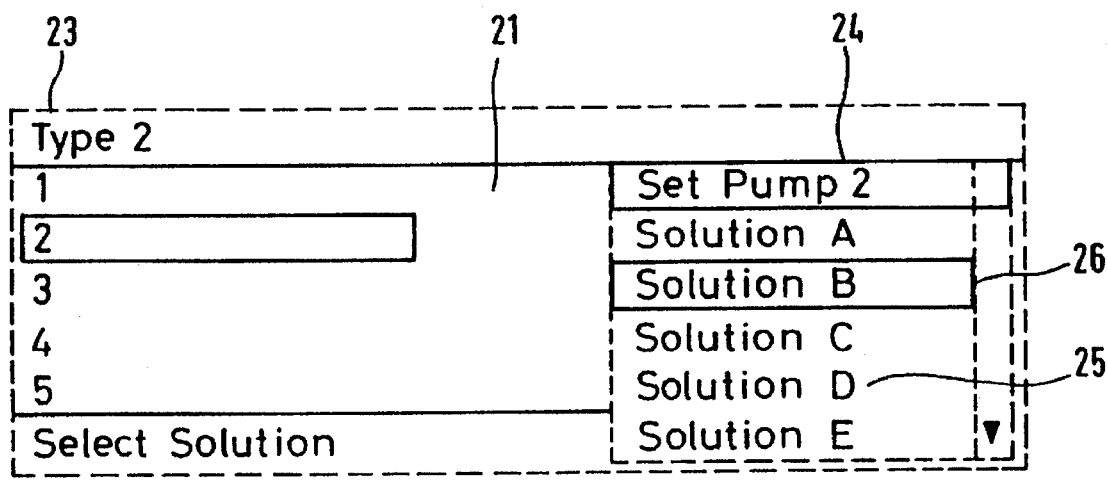
FIG. 2b shows a second menu structure with a second menu window.

FIGS. 2a and 2b show examples of the menu structures (20, 21) that can be displayed on the display screen 12. A first menu structure 20 enabling the selection of a specific configuration of the metering pumps (2, 3) includes various input values for syringes 23 in a first menu window 22. A second menu structure 21 includes a library of medications with medication input values 25 and dosage rates for medications in a second menu window 24.

The operating method of the medical apparatus according to the invention is explained below.

By means of a cursor 26, which can be moved by the rotatable knob 13, the syringe type 2 is selected as syringe input quantity 23 for the metering pump 2 within the first menu window 22 (FIG. 2a) of the first menu structure 20. By actuating the acknowledgment switch 15, the input quantity 23 is then taken into the computer unit 19. The computer unit 19 receives the second signal S2 as a control signal via the acknowledgment switch 15. At the same time, the second menu structure 21 (FIG. 2b) with the second menu window 24 is transmitted to the display screen by means of the second signal S2. Using the rotatable knob 13 and the cursor 26, an input quantity for medications 25 can be selected. The previously adopted syringe input quantity 23 appears as a setting value in the left corner of the second menu structure 21. In the case that the syringe input quantity 23 was inadvertently adopted, a return to the previous first menu structure 20 is possible by pulling the rotatable knob 13. This causes the pull switch 16 to be switched into the closed position and, by means of the first signal S1, which is transmitted to the computer unit 19, causes the return into the first menu structure 20 to be completed. At the same time, the adoption of the syringe input value into the computer unit 19 is cancelled. Using the rotatable knob 13, a new syringe input quantity 23 can now be selected and be transferred into the computer unit by activation of the acknowledgment switch 15.

In a further menu window, which is not shown in the drawings, the cursor 26 can be used to select upper and lower limit values for the dosage rate as input values (also not shown in the drawings). These limit values can then be transferred into the computer unit 19 by applying pressure to the acknowledgment switch 15. An adopted limit value can be cancelled by a pull on rotatable knob 13. Subsequently, it is possible to select a new limit value.

It is understood that the foregoing description is that of the preferred embodiments of the invention and that various changes and modifications may be made thereto without departing from the spirit and scope of the invention as defined in the appended claims.

What is claimed is:

1. A medical apparatus comprising:

a first metering device for metering a first fluid medium;

a second metering device for metering a second fluid medium;

a display device having a display screen for displaying a first menu structure including a first plurality of input quantities and a second menu structure including a second plurality of input quantities;

a computer unit for controlling said metering devices in accordance with individual ones of the input quantities from said menu structures;

a single rotary knob for selecting one of said input quantities of said first menu structure;

a pressure-actuated acknowledgment switch operatively connected to said single rotary knob so as to be actuable by said single rotary knob to issue an assuming signal (S2) for assuming the selected input quantity as a setting value for one of said metering devices;

a pull or slide switch operatively connected to said single rotary knob so as to be actuable by said single rotary knob to issue a cancelling signal (S1) for cancelling the assumption of said selected input quantity as said setting value; and, circuit means for transmitting said cancelling signal (S1) to at least one of said computer unit and said metering devices.

2. The medical apparatus of claim 1, wherein said signal (S1) causes the first one of said menu structures to be displayed on said display screen.

3. A medical apparatus comprising:

a computer unit for taking up status quantities;

a display screen for showing possible input quantities for said status quantities within a plurality of menu structures;

a single rotary knob for selecting one of said input quantities from a first one of said plurality of menu structures;

a pressure-actuated acknowledgement switch operatively connected to said single rotary knob so as to be actuable by said single rotary knob for assuming said one selected input quantity; and, a pull or slide switch operatively connected to said single rotary knob so as to be actuable by said single rotary knob to issue a cancelling signal (S1) to said computer unit for cancelling the assumption of said selected input quantity.

4. The medical apparatus of claim 3, wherein said signal (S1) causes said first one of said menu structures to be displayed on said display screen.

* * * * *